(12) United States Patent
Mirkheshty et al.

(10) Patent No.: US 8,183,051 B2
(45) Date of Patent: May 22, 2012

(54) METHOD AND SYSTEM FOR DETERMINING RESIDUAL CHLORINE OR CHLORAMINE CONCENTRATION IN SOLUTION BY COLORIMETRY

(76) Inventors: Nooshin Mirkheshty, Isfahan (IR); Sayyed Ali Alavi, Isfahan (IR)

( * ) Notice: Subject to any disclaimer, the term of this patent is extended or adjusted under 35 U.S.C. 154(b) by 121 days.

(21) Appl. No.: 12/205,879

(22) Filed: Sep. 7, 2008

(65) Prior Publication Data

US 2009/0047743 A1    Feb. 19, 2009

(51) Int. Cl.
  *G01N 21/78*  (2006.01)
  *G01N 35/00*  (2006.01)
  *G01N 21/00*  (2006.01)
  *G01N 21/75*  (2006.01)

(52) U.S. Cl. .......... 436/124; 436/43; 436/111; 436/106; 422/430; 422/50

(58) Field of Classification Search ............... 436/124, 436/43, 111, 106; 422/61, 50, 430
See application file for complete search history.

(56) References Cited

U.S. PATENT DOCUMENTS 6,087,089 A * 7/2000 Wu ................................. 435/4

OTHER PUBLICATIONS

Yoshinaga et al., Polyvinyl Alcohol as Useful Indicator on Iodometry: Volumetric and Spectrophotometric Studies on Iodine-PVA and Iodine-Starch Complexes., Analytical Sciences, Feb. 2001, vol. 17, pp. 333-337.*
Lund et al., The Influence of Disinfection Processes on Biofilm Formation in Water Distribution Systems., Wat. Res., 1995, vol. 29, No. 4, pp. 1013-1021.*

* cited by examiner

*Primary Examiner* — Christine T Mui
(74) *Attorney, Agent, or Firm* — Barry Choobin; Choobin & Choobin Consultancy

(57) ABSTRACT

A kit for determining residual chlorine or chloramine amount of a sample; comprising: a means for containing a PVA solution as an indicator, and another means for containing a reducing indicator. Said reducing indicator would be oxidized by a reaction with residual chlorine or chloramine and said PVA indicator induces a dye by reaction with oxidized compound such as free iodine; wherein intensity of said dye would be changed depending upon the residual chlorine or chloramine amount of the sample.

23 Claims, No Drawings

METHOD AND SYSTEM FOR DETERMINING RESIDUAL CHLORINE OR CHLORAMINE CONCENTRATION IN SOLUTION BY COLORIMETRY

The present invention is Sponsored by Iranian National Science Foundation and Isfahan Science and Technology Town.

FIELD OF THE INVENTION

The present invention generally relates to chemistry and health field.

BACKGROUND OF INVENTION

In order to insure that the tap water or the water in a pool or spa is safe, it must be properly sanitized to prevent any health problems arising due to such contaminants as, for example, algae, bacteria, or any other pathogens which may be in the water. To this end, excess but determinate amount of biocidal chemical systems may be used to ensure that a biocidally effective amount of water-treating agents is present in the water body.

The more commonly used biocidal agents are chlorine or chloramines containing biocides. The chlorine can be in a number of different forms, e.g., sodium hypochlorite, chlorinated isocyanurates, etc. When any of these materials interact with water, they undergo hydrolysis to form free chlorine consisting of predominantly hypochlorous acid (HOCl), which is the sanitized agent, and hypochlorite ion.

The amount of chlorine remaining in the water is referred to as "residual chlorine".

When chlorine dissolves in water, a mixture of hypochlorouse and hydrochloric acids is formed. Actually the hydrochloric acid always completely dissociates into hydrogen and chloride ions, whereas the hypochlorous acid only partially dissociates into hydrogen and hypochlorite ions. In either the hypochlorouse acid or hypochlorite ion form, chlorine is called "free chlorine residual". Free residual chlorine has a highly effective killing power toward bacteria. As it is said before, chloramine is used as biocide too.

On the other hand, the residual chlorine or chloramine in water, especially drinkable water must be controlled, because if the dosage of free chlorine or chloramine in water exceeds the standard dosage, it would be toxic.

Accordingly, it would be desirable to provide an improved method and system for determining residual chlorine or chloramine in water to ensure that the amount of residual chlorine or chloramine in water is not harmful and there is enough amount of free chlorine or chloramine in water.

On the other hand, for measuring residual chlorine amount having relatively high concentration, an iodine titration method is used. In this method, a potassium iodide solution and the test solution sample containing residual chlorine are mixed, so that isolated iodine is titrated with sodium thiosulfate. After yellow color of the solution is thinned, a starch solution is added as an indicator. The mixed solution is titrated until blue color of starch is extinguished. By the amount of sodium thiosulfate required for titration, chlorine amount can be calculated by a certain equation. However, this method is also very complicated in terms of necessitating titration operation.

Iodometry is a general method in chemistry laboratories for measuring free chlorine in solutions by titration method. Obviously this method is not suitable for preparing free chlorine kits for routine use, because the titration methods need special care, several instruments and indicators and they are time consuming. In addition, starch is not a good indicator for the kit, because its complex with free iodine produces a turbid solution that determination of the intensity of the color for users of this kit would be difficult. There are several kits that use different suitable indicators to this end. For examples, benzidine compounds and DPD (N,N-diethyl-p-phenylenediamine) have been used for this purpose. Benzidine compounds are in group of carcinogenic, toxic, irritant materials and they are dangerous for environment. DPD is also toxic and corrosive. In addition, DPD test has an important limitation due to short time stability of induced dye after reaction of indicator and residual chlorine. According to this, recommended time for measurement of intensity of induced dye is only some seconds. Even if the concentration of residual chlorine would be more excessive of standard values, induced dye will be disappeared more rapidly.

Furthermore, various enzymes such as alpha-amylase, glucosaccharase, and glucose oxidase have been used as indicators for residual chlorine assay. However, enzymes are unstable for long time storages, because of decrease in enzyme activity.

Therefore, it would have been advantageous to overcome the above shortcomings.

The present invention discloses an inexpensive kit and suitable method for determination of residual chlorine or chloramine concentration in solutions by polyvinyl alcohol (PVA) as an indicator; which is odorless, colorless and non-toxic. Stability of induced color by this kit is more than 24 h.

SUMMARY OF THE INVENTION

The present invention discloses a kit for determining residual chlorine or chloramine amount of a sample; comprising: a means for containing a PVA solution as an indicator, and another means for containing a reducing indicator. Said reducing indicator would be oxidized by a reaction with residual chlorine or chloramine and said PVA indicator induces a dye by reaction with oxidized compound such as free iodine; wherein intensity of said dye would be changed depending upon the residual chlorine or chloramine amount of the sample. Another components of said kit can be comprised: a means for mixing said indicators with the sample; a means as a color scale for calorimetric analysis having different color intensities wherein each color intensity can be represented a predetermined residual chlorine and/or chloramine amount of the test solution; so that said residual chlorine or chloramine amount of the sample would be determined by comparing the intensity of said induced dye to said color scale. Color scale can be stored in a device such as a calorimeter and a software could be used to compare.

In another embodiment, the present invention discloses a method for determining residual chlorine or chloramine amount of a sample, comprising steps: containing a source of PVA in form of solution as an indicator; mixing said indicator and a reducing indicator such as a iodide source with the sample wherein said mixing creates a color intensity depending on the residual chlorine or chloramine amount of sample; measuring the color intensity by comparing said created color intensity to a predetermined series of color indicators with different color intensities representing concentration amount of residual chlorine or chloramine in solutions, or by a calorimeter which saved different predetermined color intensities for this propose.

DETAILED DESCRIPTION OF THE PREFERRED INVENTION

The present invention is directed to a method and system for determining residual chlorine or chloramine amount of a sample. Generally, the solutions to be tested can be comprised, for example, drinking water, pool water and the like.

For one of the specific embodiments, the present invention discloses a kit which comprises:

(a) A means for at least containing a source of PVA in form of solution for preparation of an indicator, and a means for at least containing a source of a reducing indicator may be applied in any suited form, such as for example liquid, powder, tablet, etc, for preparation of another indicator. For the salt of the reducing indicator, for example, sodium salt or potassium salt of the reducing compounds can be mentioned. In the above mentioned salts, in a case where the reducing indicator is an iodide compound, the compound becomes to be potassium iodide or sodium iodide, both of which are preferable in the present invention, more preferred the first compound.

The solvent used in this case may be any one as long as it can dissolve any of said two indicators. For example, it may be either a non-protic organic solvent such as dimethyl sulfoxide (DMSO) or a protic organic solvent such as dimethyl formamide (DMF) or a lower alcohol. Also, it may be an aqueous acidic solution. Preferably, an aqueous solution of an organic solvent such as acetic acid or a thin aqueous solution of a mineral acid such as a diluted hydrochloric acid solution with pH 4.0 may be used for reducing indicator and an aqueous solution for PVA.

The indicators for determining of residual chlorine or chloramine amount may be prepared by adding a pre-determined amount of any of these solutions to a buffer solution. In this case, pH of the solution can be regulated within a range in which the indicator is not precipitated. Preferred pH is 1 through 7, more preferred is 2 through 5 and, most preferred is 2 through 4. For the buffer system used herein, although there is no specific limitation, however, for example, malonic acid, phthalic acid, fumaric acid, tartaric acid, citric acid, β-alanine, dimethylglutaric acid, aspartic acid, barbituric acid, benzoic acid, succinic acid, oxalic acid, acetic acid, malic acid, 2-(N-morpholino)ethane sulfonic acid and maleic acid, etc. can be used. By adding a solution containing residual chlorine or chloramine, for example, by adding one tenth of the total quantity of an aqueous hypochlorous acid solution, which is diluted into adequate magnification, coloration in slightly purple through deep purple takes place, ranging from samples with lower residual chlorine or chloramine concentration to samples of higher concentration.

To be more specific, density of coloration has a positive correlation with the concentration of residual chlorine or chloramine with respect to the intensity of mentioned color.

PVA indicator solution concentration can be regulated within a range in which PVA solution can be flowed. Preferably, it is 0.1 wt.-% through 15 wt.-%, more preferably 1 wt.-% through 10 wt.-%, most preferably 2 wt.-% through 7.5 wt.-%. Concentration of said reducing indicator such as the iodide salt can be regulated within a range in which reducing indicator is not precipitated. Preferably, it is 0.01 M through 10 M and more preferably 0.1 M through 5 M.

(b) A means at least for mixing said indicators with the sample;

(c) a means at least for non-automatically, semi-automatically or automatically colorimetric analysis having plural different sample color intensities wherein each of said different sample color intensities represents a different residual chlorine or chloramine amount so that said residual chlorine or chloramine amount of said sample can be determined by comparing an intensity of said dye with said plural different sample color intensities; and wherein said automatic or semi-automatic means such as a colorimeter but not limited to this instrument, compares intensity of said dye to a saved plural different sample color intensities related to the concentration of residual chlorine or chloramine in solution, so that said residual chlorine or chloramine amount of said sample can be determined.

Above means can be placed in a box as a container.

Particularly, quantitative determination by visual observation of color intensity or by measurement of absorbance becomes possible. By measuring the degree of light absorbance, preferably at a wavelength between 425-575 nm, more preferably 450-550 nm, most preferably 480-500 nm, using a spectrophotometer of the solution to be tested can appropriately be measured by comparing residual chlorine or chloramine concentration (for example, a residual chlorine or chloramine calibration curve) which had been determined in advance.

In another embodiment the present invention discloses a kit which comprises:

The kit instruction manual can comprise the following instructions:
  Wash the container with the test solution sample;
  Fill the container with the test solution sample to a predetermined level;
  Add 5 drops of iodide solution and 10 drops of PVA solution;
  Cap the container and overturn it for several times;
  Compare intensity of induced dye to the predetermined series of color indicators;
  Determine residual chlorine amount of the test solution sample based on first group of predetermined values, and determine chloramine amount based on second group of predetermined values;
  Wash the container for the next use.

In another embodiment the present invention discloses a kit which comprises said two indicators in forms of solution in a same container.

In another embodiment the present invention discloses a method for determining residual chlorine or chloramine amount of a sample wherein said method comprises steps of:

(a) Applying a means at least for containing a source of PVA in form of solution for preparation of an indicator, and a means for containing a source of a reducing indicator may be applied in any suited form, such as for example liquid, powder, tablet, etc, for preparation of another indicator. For the salt of the reducing indicator, for example, sodium salt or potassium salt of the reducing compounds can be mentioned. In the above mentioned salts, in a case where the reducing indicator is an iodide compound, the compound becomes to be potassium iodide or sodium iodide, both of which are preferable in the present invention, more preferred the first compound.

The solvent used in this case may be any one as long as it can dissolve any of said two indicators. For example, it may be either a non-protic organic solvent such as dimethyl sulfoxide (DMSO) or a protic organic solvent such as dimethyl formamide (DMF) or a lower alcohol. Also, it may be an aqueous acidic solution. Preferably, an aqueous solution of an organic solvent such as acetic acid or a thin aqueous solution of a mineral acid such as a diluted hydrochloric acid solution with pH 4.0 may be used for reducing indicator and an aqueous solution for PVA.

The indicators for determining of residual chlorine or chloramine amount may be prepared by adding a pre-determined amount of any of these solutions to a buffer solution. In this case, pH of the solution can be regulated within a range in which the indicator is not precipitated. Preferred pH is 1 through 7, more preferred is 2 through 5 and, most preferred is 2 through 4. For the buffer system used herein, although there is no specific limitation, however, for example, malonic acid, phthalic acid, fumaric acid, tartaric acid, citric acid, β-alanine, dimethylglutaric acid, aspartic acid, barbituric acid, benzoic acid, succinic acid, oxalic acid, acetic acid, malic acid, 2-(N-morpholino)ethane sulfonic acid and maleic acid, etc. can be used. By adding a solution containing residual chlorine or chloramine, for example, by adding one tenth of the total quantity of an aqueous hypochlorous acid solution, which is diluted into adequate magnification, coloration in slightly purple through deep purple takes place, ranging from samples with lower residual chlorine or chloramine concentration to samples of higher concentration.

To be more specific, density of coloration has a positive correlation with the concentration of residual chlorine or chloramine with respect to the intensity of mentioned color.

PVA indicator solution concentration can be regulated within a range in which PVA solution can be flowed. Preferably, it is 0.1 wt.-% to 15 wt.-%, more preferably 1 wt.-% through 10 wt.-%, most preferably 2 wt.-% through 7.5 wt.-%. Concentration of said reducing indicator such as the iodide salt can be regulated within a range in which reducing indicator is not precipitated. Preferably, it is 0.01 M through 10 M and more preferably 0.1 M through 5 M.

(b) Applying a means at least for mixing said indicators with the sample;

(c) Applying a means at least for non-automatically, semi-automatically or automatically colorimetric analysis having plural different sample color intensities wherein each of said different sample color intensities represents a different residual chlorine or chloramine amount so that said residual chlorine or chloramine amount of said sample can be determined by comparing an intensity of said dye with said plural different sample color intensities; and wherein said automatic or semi-automatic means such as a calorimeter but not limited to this instrument, compares intensity of said dye to a saved plural different sample color intensities related to the concentration of residual chlorine or chloramine in solution, so that said residual chlorine or chloramine amount of said sample can be determined.

In another embodiment the present invention discloses a method for determining residual chlorine and chloramine of a test sample wherein said method comprises steps of previous disclosed method but by applying a means for containing said two indicators in one container.

Generally, excess source of the reducing indicator and PVA indicator can be added to the sample. In this step, residual chlorine or chloramine oxidizes the reducing indicator. Then oxidized compound such as iodine, binds to PVA and produces a colored complex in solution. The color of the solution would be purple. By comparing the intensity of the color of this solution to predetermined series of color indicators of residual chlorine or chloramine, the concentration of free residual chlorine or chloramine could be estimated.

For preparation of the color scale, chlorine or chloramine solutions with determined concentrations would be needed. These standard solutions can be tested with the indicators of the kit, and then according to the intensity of the color of each solution, a color spectrum could be prepared by paper or plastic or glass or the like. This spectrum with plural concentrations that are written near each color could be fixed beside the mixing container.

For preventing the microorganism growth in indicator containers, the present inventors have found that sodium azide or other preservative material, which doesn't interfere in test, can be suitable. For example, sodium azide can be used preferably in range of 1-3 mM.

As disclosed by inventors, determined concentration of residual chlorine in the test solution by said kit and method is preferably 0.02 mg/L through 30 mg/L and more preferably 0.05 mg/L through 20 mg/L and most preferably 0.1 through 15 mg/L.

As explained above, an important advantage of the claimed kit in comparison with DPD test is its long duration of color stability. Determination of residual chlorine or chloramine amount of sample by present disclosed method and kit becomes possible even after the laps of the time of 24 hours; however color of the reagent in DPD test changes in a few minutes or even in a few seconds. This is very important for accuracy of measurements by examiners.

The form of containers may be anything which can be tightly sealed. However, test tube types are preferably employed.

The physical properties of the material of the containers is preferably 0.01 through 0.06% in terms of moisture-absorbance property, $CO_2$: 50 through 900 ml/100 m 2/mm/24 hr atm at 25° C. and $O_2$: 50 through 350 ml/100 m 2/24 hr atm at 25° C. in terms of gas transmissivity. More specifically, for example, polyethylene can be mentioned.

Any form of a lid tightly closing the containers of the present invention may be used. Petcock and tape-seal types are preferable. Specifically, the tape-sealed type is preferable.

The physical property of the material of the lid is, for example, in the case of polymers such as polyethylene, polypropylene, polyvinyl chloride, polyvinylidene chloride, polytetrafluoroethylene, polyester and polyethylene terephthalate, 1.1 through 2.2 kg/cm 2 in terms of tensile strength, 10 through 600% in terms of extension breakage and 1.1 through 25 kg/mm 2 in terms of internal tearing strength.

In the case of aluminum foil, tensile strength is preferably 10 through 90 N/mm 2, extension breakage is preferably 2 through 45% and internal tearing strength is preferably 5 through 60 kg/mm 2.

The moisture absorbance property of the above-mentioned lid is preferably 0 through 9%. Its gas transmissivity is preferably $CO_2$: 1.5 through 2700 ml/100 m 2/mm/24 hr atm at 25° C. and $O_2$: 20 through 2000 ml/100 m 2/24 hr atm at 25° C.

The lids can be sealed onto the containers by means of heat, electromagnetic waves, ultrasonic waves, laser beams or adhesive agents. When they are sealed by means of heat, electromagnetic waves, ultrasonic waves or laser beams, may be used with which the lids can be sealed to the containers for 1 second at 150 through 160° C. In the case of an adhesive agent, if it is a plane adhesion, it can be sealed to resist 2 kg/cm 2.

In the case of the present invention, it is preferable to seal them with heat or laser beams from viewpoint of tight sealing property and producibility.

With regard to the constitution of the lids and the containers of the kit for determining the indicators, the lids are preferably a complex sheet wherein an aluminum foil and a polymer (for example, polyethylene) and the containers are preferably test tubes made of polystyrene.

In addition, in a complex sheet wherein an aluminum foil and polymer are sealed, the thickness of polymer is preferably 1 μm through 10 μm, and aluminum is preferably 5 through 50 μm provided that aforesaid sheet is not broken by means of a chip used for injection machine which injects a sample solution (an oxidized product).

For load when breaking a sealed aluminum sheet, in the case of chip for 200 μl for a common-use injecting machine, it is sufficient to be 50 g/m 2 or more and 200 g/m 2 or more is necessary to ensure against water leakage.

In addition, the thickness of the above-mentioned test tubes made by polystyrene are ordinarily 200 through 2000 μm, and preferably 600 through 1300 μm.

The kit for determining residual chlorine or chloramine amount of the present invention can be utilized for anything. Among them, it is suitable for determining residual chlorine or chloramine amount.

The following non-limiting example is illustrative of the kit of the present invention.

Example

Below, the present invention is further explained with reference to working example; however the scope of the present invention is not limited by this example.

Analytical grade potassium iodide and sodium hypochlorite were commercially obtained from Merck and industrial PVA (n=500, 1000, 1500, 200; s.d.=86-90%, ave. 88%) was used.

To prepare PVA solution 5%, 5 g of PVA was dissolved in 100 ml distilled water. According to difficult solubility of PVA in water, the mixture of PVA and distilled water was heated by heater till 85° C. and was stirred during 3-5 hours continuously with electromagnetic stirrer to prepare a uniform solution.

Preparation of the residual chlorine was performed in the following manner using sodium hypochlorite powder. A solution of 0.0265 g of sodium hypochlorite powder in 100 ml distilled water was prepared. For determining the concentration of the free chlorine in solution, the iodometry method was used. The concentration of free chlorine in foresaid solution was 50 mg/L. This stock solution was diluted with distilled water to prepare solutions of which total chlorine amounts were 0.1 (mg/l), 0.2 (mg/l), 0.3 (mg/l), 0.5 (mg/l), 0.6 (mg/l), 1 (mg/l), 1.5 (mg/l), 2 (mg/l), 3 (mg/l), 3.5 (mg/l), 4 (mg/l), 5 (mg/l), 10 (mg/l), 15 (mg/l), 20 (mg/l), and 25 (mg/l), respectively.

The preparation of chlorine standard solutions is shown in table 1.

TABLE 1

| Final Chlorine solution Concentration (mg/l) | Chlorine stock solution volume (ml) |
|---|---|
| .1 | 0.05 |
| 0.3 | 0.15 |
| 0.5 | 0.25 |
| 1 | 0.5 |
| 2 | 1 |
| 3.5 | 1.75 |
| 4 | 2 |
| 5 | 2.5 |
| 10 | 5 |
| 15 | 7.5 |
| 20 | 10 |
| 25 | 12.5 |

Then 10 ml of each sodium hypochlorite solution was added to the mixing container and 5 drops of potassium iodide and 10 drops of PVA solution (5%) were added to the above solution. The solution was shaken gently. After 2-3 seconds, the color would appear. Intensity of the color was stable for several hours. Color intensities were visually observed. The results are shown in table 2. The color of the solutions was simulated by Photoshop software, and after printing, a spectrum of colors that their intensities depended on chlorine concentrations were prepared. Then the intensity of the color of unknown solution was compared optically with this color spectrum and the free chlorine concentration was estimated.

TABLE 2

| Total chlorine amount (mg/l) | Observed color |
|---|---|
| 0.1 | Slightly purple |
| 0.3 | Slightly Purple |
| 0.5 | Pale Purple |
| 1 | Purple |
| 2 | Purple |
| 3.5 | Purple |
| 4 | Purple |
| 5 | Deep Purple |
| 10 | Deep Purple |
| 15 | Deep Purple |
| 20 | Deep Purple |

It will be understood that various modifications may be made to the points disclosed here in. Therefore the above description should not be construed as limiting for this kit, but merely as exemplification of preferred embodiments. Other arrangement and methods may be implemented by those skilled in the art without departing from the scope and the spirit of this invention. Moreover, those skilled in the art will envision other modification within the scope and spirit of the claims appeared hereto.

What is claimed is:

1. A kit for determining residual chlorine or chloramine amount in a sample wherein said kit comprises a means for containing an iodide indicator solution for preparation of a first indicator and wherein said iodide indicator solution includes an iodide compound and a buffer solution, and wherein concentration of iodide in said iodide indicator solution is in a range of 0.01M to 10 M and wherein said buffer solution has a pH of 2-4;

a means for containing a polyvinyl alcohol solution for preparation of a second indicator and wherein said polyvinyl alcohol solution includes a source of polyvinyl alcohol and said buffer solution, and wherein concentration of polyvinyl alcohol in said polyvinyl alcohol solution is in a range of 2 wt.-% to 7.5 wt.-% and wherein said buffer solution has a pH of 2 to 4 so that the polyvinyl alcohol indicator solution is flowed;

a means for mixing said first indicator and said second indicator with a sample, and wherein said mixing forms a dye and wherein a color intensity of said dye depends upon an amount of residual chlorine or chloramine present in said sample;

a means for colorimetric analysis non-automatically or semi-automatically or automatically with plural different sample color intensities and wherein each of said different sample color intensities represents a mutually different residual chlorine or chloramine amount so that said residual chlorine or chloramine amount of said sample is determined by comparing an intensity of said dye with said plural different sample color intensities, and wherein said residual chlorine amount of said sample is within a range of 0.02 mg/L-30 mg/L;

an instruction manual with instruction for using said kit;

wherein said kit comprises an effective amount of said polyvinyl alcohol for preparation of an indicator to provide a color stability for a long duration wherein the long duration is more than 24 hours and wherein said effective amount is within 2 wt.-% to 7.5 wt.-%.

2. The kit as claimed in claim 1, wherein said kit comprises at least a means for containing a source of a reducing agent for preparation of a reducing indicator, and a source of polyvinyl alcohol in form of a solution for preparation of another indicator and wherein said reducing agent being oxidized by a residual chlorine or chloramine and wherein said PVA indicator forming a dye by a reaction with the oxidized compound and wherein an intensity of said dye being changed depending upon the residual chlorine or chloramine amount of said sample; wherein a solvent is used for dissolving the reducing indicator and wherein said said solvent is a non-protic organic solvent or a protic organic solvent and wherein said non-protic organic solvent includes dimethy sulfoxide (DMSO) and wherein said protic organic solvent includes dimethyl formamide (DMF) or a lower alcohol and an aqueous acidic solution.

3. The kit as claimed in claim 2, wherein said source of reducing agent is an iodide containing compound as an iodide indicator.

4. The kit as claimed in claim 2, wherein said kit comprising:
(a) a means for containing an iodide indicator and a polyvinyl alcohol indicator, wherein all said indicators are mixed-with said sample; wherein said intensity of said dye being changed depending upon the concentration of the residual chlorine or chloramine in said sample;
(b) a means for scaling colors non-automatically, semi-automatically, automatically for a colorimetric analysis having a plurality of predetermined color intensities wherein each of said predetermined color intensity represents different residual chlorine or chloramine amount of said sample so that the residual chlorine or chloramine amount of said sample is determined by comparing said intensity of said dye with said predetermined color intensities;
and wherein said means for scaling colors is a color scale and wherein said color scale is stored in a device and wherein said device is a colorimeter and wherein colorimeter is saved with different predetermined color intensities and wherein a software is provided to compare said intensity of said dye with said predetermined color intensities automatically.

5. The kit as claimed in claim 1, wherein said sample is selected from a group comprising of pool water or drinking water.

6. The kit as claimed in claim 3, wherein said iodide containing compound is an iodide salt.

7. The kit as claimed in claim 6, wherein said iodide salt is selected from a group comprising: potassium iodide, sodium iodide or mixture thereof.

8. The kit as claimed in claim 3, wherein said iodide indicator is applied in a form of solid.

9. The kit as claimed in claim 3, wherein said iodide indicator is applied in a form of solution and wherein said solution having a concentration level.

10. The kit as claimed in claim 3, wherein said indicators are at least in one container.

11. The kit as claimed in claim 1, wherein the polyvinyl alcohol indicator is applied in a form of solution and wherein concentration of said solution is in the range of 1 wt.-% to 10 wt.-%.

12. The kit as claimed in claim 11, wherein said concentration of said solution is in the range of 2 wt.-% to 7.5 wt.-%.

13. The kit as claimed in claim 9, wherein said concentration level is in the range of 0.01 M to 10M.

14. The kit as claimed in claim 13, wherein said concentration level is in the range of 0.1 M to 5M.

15. The kit as claimed in claim 2, wherein at least one preservative compound is used for preventing a micro-organic growth in at least one of said indicators and wherein said preservative compound doesn't interfere with determining residual chlorine or chloramine in said sample.

16. The kit as claimed in claim 15, wherein said preservative compound is sodium azide in the range of 1 mM to 3 mM.

17. The kit as claimed in claim 1, wherein said kit comprises a means for manually determining residual chlorine or chloramine amount of said sample by comparing the intensity of said dye with said plural different sample color intensities wherein said means for manually determining residual chlorine or chlorine amount is a color scale.

18. The kit as claimed in claim 1, wherein said kit comprises a means for semiautomatically determining residual chlorine or chloramine amount of said sample by comparing the intensity of said dye with said plural different sample color intensities.

19. The kit as claimed in claim 1, wherein said kit comprises a means for automatically determining residual chlorine or chloramine amount of said sample by comparing the intensity of said dye with said plural different sample color intensities and wherein said means for automatically determining residual chlorine or chloramine amount of said sample is a calorimeter.

20. A method for determining residual chlorine or chloramines amount of a sample, comprising steps of:
applying a polyvinyl alcohol in form of a solution to a sample as an indicator;
applying a source of a reducing agent such as an iodide source to the sample for preparation of a reducing indicator;
mixing the polyvinyl alcohol and the reducing indicator with the sample; wherein said mixing oxidizes said reducing agent by said residual chlorine or chloramines of the sample to form an oxidized compound; wherein the polyvinyl alcohol reacts with the oxidized compound to form a dye; wherein a color intensity of said formed dye is changed depending upon the residual chlorine or chloramine amount of the sample; and
determining said residual chlorine or chloramine amount from said color intensity of said formed dye.

21. The method as claimed in claim 20, wherein said steps of determining said residual chlorine or chloramine amount from said color intensity of said formed dye involves measuring said color intensity by comparing said color intensity to a predetermined series of color indicators with different color intensities representing concentration amount of residual chlorine or chloramine in solutions, or by a colorimeter which saved different predetermined color intensities.

22. The method as claimed in claim 20, wherein at least one part of said method is performed automatically by an automatic means wherein said automatic means is a colorimeter.

23. The method as claimed in claim 20, wherein at least one part of said method is performed manually.

* * * * *